United States Patent [19]

Barreras, Sr. et al.

[11] Patent Number: 5,735,887
[45] Date of Patent: Apr. 7, 1998

[54] CLOSED-LOOP, RF-COUPLED IMPLANTED MEDICAL DEVICE

[75] Inventors: Francisco Jose Barreras, Sr.; Robert Echarri, both of Miami, Fla.

[73] Assignee: Exonix Corporation, Miami, Fla.

[21] Appl. No.: 763,000

[22] Filed: Dec. 10, 1996

[51] Int. Cl.⁶ .................. A61N 1/00; H04B 7/00
[52] U.S. Cl. .................. 607/60; 607/32; 607/33; 607/61; 128/903
[58] Field of Search .................. 607/29, 30–34, 607/60, 61, 2; 128/903

[56] References Cited

U.S. PATENT DOCUMENTS

| | | |
|---|---|---|
| 3,209,081 | 9/1965 | Ducote et al. . |
| 3,920,025 | 11/1975 | Stasz et al. . |
| 3,942,535 | 3/1976 | Schulman . |
| 4,024,875 | 5/1977 | Putzke . |
| 4,026,301 | 5/1977 | Friedman et al. . |
| 4,041,955 | 8/1977 | Kelly et al. . |
| 4,071,032 | 1/1978 | Schulman . |
| 4,096,866 | 6/1978 | Fischell . |
| 4,102,344 | 7/1978 | Conway et al. . |
| 4,142,533 | 3/1979 | Brownlee et al. . |
| 4,197,850 | 4/1980 | Schulman et al. . |
| 4,203,448 | 5/1980 | Keller, Jr. . |
| 4,408,608 | 10/1983 | Daly et al. . |
| 4,441,498 | 4/1984 | Nordling . |
| 4,459,989 | 7/1984 | Borkan . |
| 4,532,930 | 8/1985 | Crosby et al. . |
| 4,612,934 | 9/1986 | Borkan . |
| 4,741,339 | 5/1988 | Harrison et al. . |
| 4,793,353 | 12/1988 | Borkan . |
| 5,168,871 | 12/1992 | Grevious . |
| 5,193,539 | 3/1993 | Schulman et al. . |
| 5,237,991 | 8/1993 | Baker, Jr. et al. . |
| 5,312,439 | 5/1994 | Loeb . |
| 5,314,457 | 5/1994 | Jeutter et al. . |
| 5,324,316 | 6/1994 | Schulman et al. . |
| 5,350,413 | 9/1994 | Miller . |
| 5,358,514 | 10/1994 | Schulman et al. . |
| 5,405,367 | 4/1995 | Schulman et al. . |
| 5,476,488 | 12/1995 | Morgan et al. ................ 607/32 |
| 5,531,774 | 7/1996 | Schulman et al. . |
| 5,562,714 | 10/1996 | Grevious . |

*Primary Examiner*—William E. Kamm
*Assistant Examiner*—Kennedy J. Schaetzle
*Attorney, Agent, or Firm*—Thomas R. Vigil

[57] ABSTRACT

The implantable, electrically operated medical device system comprises an implantable radio frequency (RF) receiver and an external RF transmitter. The receiver has a receiving antenna and electronic circuitry coupled to the receiving antenna and includes a microcontroller having an output, a non-volatile memory coupled to the microcontroller and an implanted, electrically and autonomously operated medical device is coupled to the output of the microcontroller. The external RF transmitter has a power source and a transmitting antenna. The receiver further includes circuitry coupled to the microcontroller for regulating the power transmitted by the transmitter, whereby, RF energy can be transmitted by the transmitter and coupled into the receiver and the level of RF energy transmitted by the transmitter is controlled by the circuitry. The transmitter is also used to: a) program into the memory of the implanted device (receiver) its operating values; b) start and stop delivery of medical therapy by the implanted device, c) interrogate the operating values of the implanted device, and d) interrogate physiological parameters which are measured by the implanted device.

25 Claims, 5 Drawing Sheets

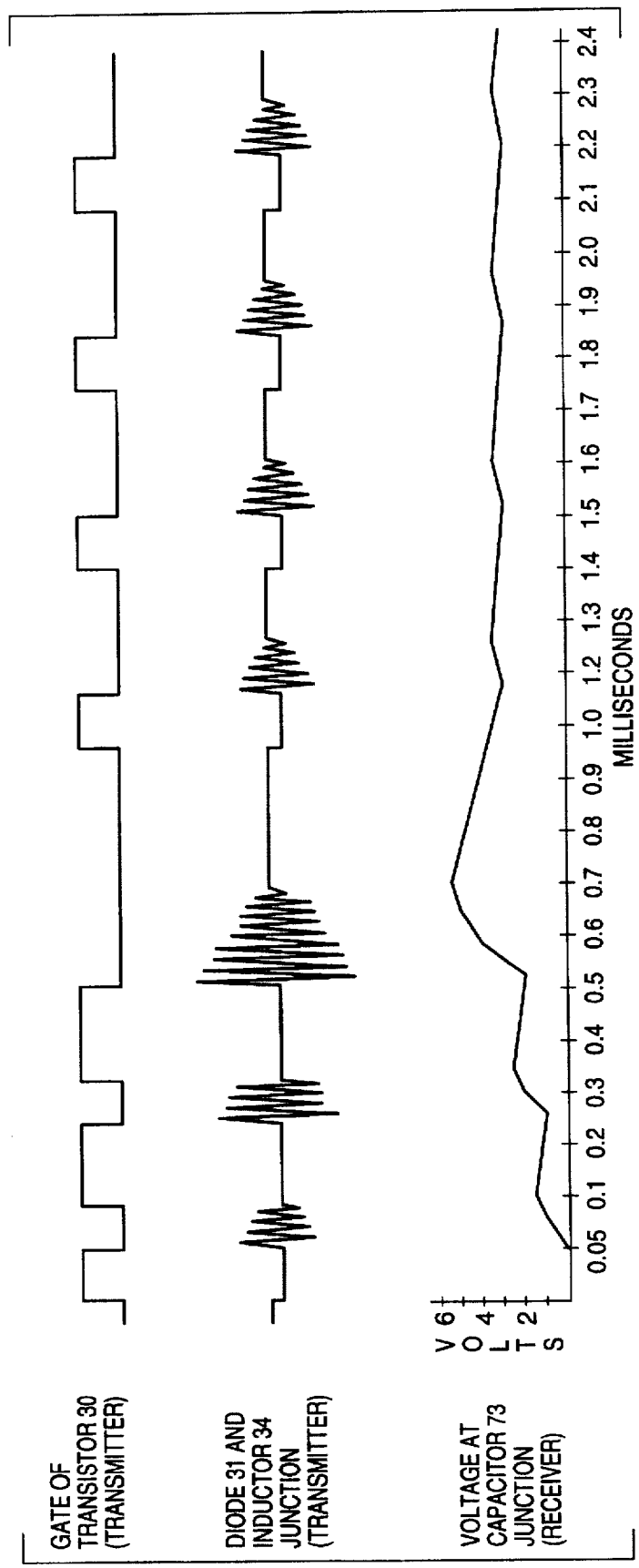

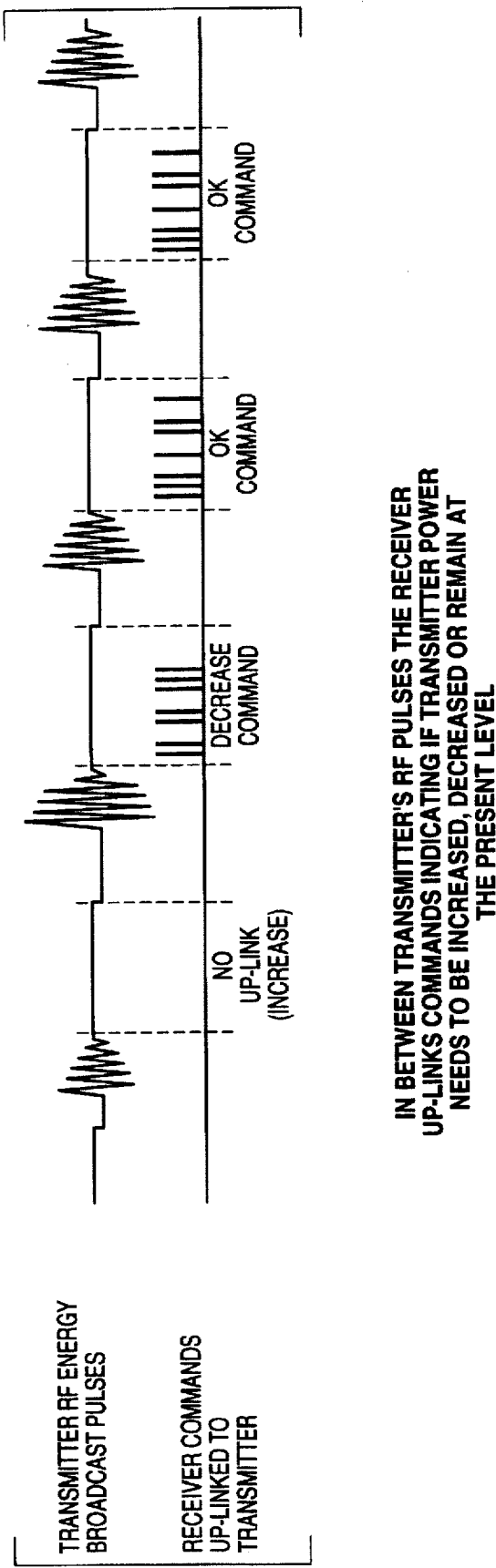

CLOSED-LOOP, RF-COUPLED IMPLANTED MEDICAL DEVICE

BACKGROUND OF THE INVENTION

1. Field of the Invention

The present invention is directed to a closed-loop, controlled RF-coupled implanted medical device.

2. Description of the related art including information disclosed under 37 CFR §§ 1.97–1.99.

The concept of using implantable, electrically operated medical devices for treating specific diseases or physical disorders is well known. Examples of implantable, electrically operated medical devices are: cardiac pacemakers which restore a sick human heart to a normal rhythm, neural stimulators which control nerve or brain response (such as pain or epileptic seizures), infusion pumps for subcutaneously drug delivery (such as an insulin pump), defibrillators for treating heart fibrillations and diagnostic devices for monitoring specific physiological parameters.

The use of RF coupled, implantable, electrically operated medical devices has been well established for a number of years, especially for the control of nerve or brain response to treat intractable pain, epileptic seizures and tremors as a result of Parkinson disease. An example of prior art RF coupled devices is a neural stimulator system comprising an external transmitter and a surgically implanted receiver. The RF transmitter generates a radio frequency carrier which is modulated twice for each stimulus pulse, first to designate to the receiver which electrodes are to be used to deliver the stimulus pulse and their respective polarity, and secondly, the amplitude of the carrier is modulated for a period corresponding to the stimulus pulse width, the peak modulated voltage representing the pulse amplitude. The amplitude of the stimulation pulse delivered by the receiver is proportional to the peak value of the RF signal received during the stimulation portion of the carrier wave form. The frequency of stimulation is controlled by the RF transmitter by simply adjusting the repetition rate of the modulation.

A flaw with this prior device is that the actual amplitude of the stimulus pulse delivered by the receiver varies as a function of coupling distance and alignment between the transmitting and receiving antennas. When the stimulation amplitude is adjusted at the transmitter to couple a specific amplitude at the receiver with a certain distance and alignment, if this coupling distance or alignment is later altered (i.e. when the patient repositions the transmitting antenna over the implant site after taking a shower), the stimulation amplitude may change, possibly causing discomfort (if over stimulation) or ineffective therapy (if under stimulation).

Another deficiency often encountered with prior devices is that the RF transmitter unit broadcasts at a relatively high constant power in order to guarantee that enough power is always coupled to power the receiver within a substantial range of receiver power consumption requirements and antenna coupling distances. This means that at a relatively short coupling distance where good RF power coupling is possible and/or at low stimulation values resulting in low receiver power needs, the transmitter is broadcasting with the same high RF power required for long coupling distances and high receiver power needs. Obviously, this results in very short transmitter battery life requiring battery replacement every one to three days at a great expense to the patient.

Still another deficiency often encountered with prior devices occurs when a patient walks into a strong electromagnetic interference (EMI) field. Since the electrode and polarity values are transmitted to the receiver just prior to each stimulus pulse, if the EMI is of sufficient magnitude it may interfere with the transmission resulting in improper or loss of stimulation.

Several examples of previously proposed analogous and non-analogous programmable stimulators and/or RF coupled/powered stimulators are disclosed in the following U.S. patents:

| U.S. Pat. No. | Patentee |
| --- | --- |
| 3,209,081 | Ducote |
| 3,920,025 | Stasz et al. |
| 3,942,535 | Schulman |
| 4,024,875 | Putzke |
| 4,026,301 | Friedman et al. |
| 4,041,955 | Kelly et al. |
| 4,071,032 | Schulman |
| 4,096,866 | Fischell |
| 4,102,344 | Conway et al. |
| 4,197,850 | Schulman et al. |
| 4,203,448 | Keller |
| 4,408,608 | Daly, et al. |
| 4,441,498 | Nordling |
| 4,459,989 | Borkan |
| 4,532,930 | Crosby et al. |
| 4,612,934 | Borkan |
| 4,741,339 | Harrison et al. |
| 4,793,353 | Borkan |
| 5,168,871 | Grevious |
| 5,193,539 | Schulman et al. |
| 5,237,991 | Baker et al. |
| 5,312,439 | Loeb |
| 5,314,457 | Juetter et al. |
| 5,324,316 | Schulman et al. |
| 5,350,413 | Miller |
| 5,358,514 | Schulman |
| 5,405,367 | Schulman |
| 5,531,774 | Schulman et al. |
| 5,562,714 | Grevious |

The Ducote U.S. Pat. No. 3,209,081 discloses an implant with power supplied to amplifier transistors of an implanted radio receiver from a power transmitter. The electrical potential delivered through the RF signal is stored in a capacitor. Voltage is applied to that capacitor continuously and constantly as long as the power transmitter is functioning.

The Stasz et al. U.S. Pat. No. 3,920,025 discloses a body stimulation system including a remote low frequency transmitter, a low frequency receiver, a power transmitter controlled by the low frequency receiver, and an implantable stimulator device with means for receiving signals from the power transmitter. The power signal is synchronized to the low frequency transmitter, and interference protection circuitry is included in the system. Special circuitry is also provided to decrease the effect of the spacial relationships between the power antenna and the implanted receiver.

The Schulman U.S. Pat. No. 3,942,535 discloses a rechargeable tissue stimulating system with a telemetry controlled power source. A constant current power source acting through an induction coil externally located with respect to a living patient is used to induce current flow in a charging circuit located beneath the skin of the patient. The charging circuit, in turn, recharges a battery which powers an electronic generator used for applying electrical pulses to stimulate living tissue in order to maintain bodily functions in the patient. A telemetry circuit connected to the charging circuit provides a magnetic output signal controlling externally located means associated with the power source. Such external means in response to this signal modulate the strength of the charging magnetic field, as well as provide visual or audio indication of proper charging as well as the proper positioning of the external power source with respect to the implanted charging circuit, completion of the proper charging interval to restore the amount of current used, and improper charging.

The Putzke U.S. Pat. No. 4,024,875 discloses a device for the non-invasive programming of an implantable body stimulator. The device includes a power supply and circuitry for generating and transmitting a preselected number of pulses of radio frequency energy. A push-button switch initiates the operation of the pulse-generating circuitry and the power supply is enabled only during an interval of predetermined duration following the initiating of operation of the pulse-generating circuitry. The power supply can include a power source, such as batteries, and a voltage regulator for establishing a substantially constant supply voltage for all power source voltages above a preselected level. The device may include circuitry for indicating the establishment of the substantially constant supply voltage as well as circuitry for preventing the transmission of any programming pulses upon a failure to establish the substantially constant supply voltage level. The transmitted pulses may be employed to alter an output parameter of any implanted body stimulator and is described with reference to an alteration in the repetition rate of an implanted cardiac pacemaker.

The Friedman et al. U.S. Pat. No. 4,026,301 discloses implanted electrodes that are connected by leads to a receiver circuit implantable beneath the patient's skin and operable to receive RF modulated stimulation impulses transmitted through the skin. The impulses are developed by a patient operated RF transmitter with a cyclic on and off stimulation and rest periods so that stimulation of the muscles may take place while the patient relaxes or sleeps.

The Kelly et al. U.S. Pat. No. 4,041,955 discloses an implantable hermetically sealed living tissue stimulator which includes a coil in which current is induced by an external alternating magnetic field. All the stimulator circuit components except for one or more electrode leads are hermetically sealed within a hermetic container formed of a biocompatible metal.

The Schulman U.S. Pat. No. 4,071,032 discloses an implantable living tissue stimulator having a current conductive protective shield, to prevent the flow of currents to or from the stimulator circuitry via the electrically conductive body fluid. The stimulator can be of the rechargeable type in which the stimulator circuit components are surrounded by a pickup coil, designed to pick up an external magnetic field for recharging the power source, e.g., battery of the stimulator. Ferrite slabs can extend through the coil wound about the rest of the stimulator components, in order to increase the coil pick up efficiency and to divert the magnetic field from the stimulator metal components, such as a metal container in which the stimulator circuitry is hermetically sealed and thereby minimize the heating of the components and/or the metal container.

The Fischell U.S. Pat. No. 4,096,866 discloses an implanted tissue stimulator apparatus comprising circuitry, powered by an implanted rechargeable battery, to produce electrical stimulation and apply it to selected body tissue. The condition of the rechargeable battery is monitored continuously and if the cell fails or its voltage drops below a preselected level, the stimulator reverts to a stand-by power source provided by a battery having an extremely long shelf-life. Logic circuitry within the implanted stimulator monitors the operation of a pulse generator, in addition to the condition of the rechargeable battery, and if faulty operation of the pulse generator is detected the logic circuitry automatically switches to the back-up pulse generator in order to maintain adequate tissue stimulation.

The Conway et al. U.S. Pat. No. 4,102,344 discloses an implantable device that is activated and powered exclusively by an external high frequency transmitter. The implanted device includes two separate storage capacitors which provide two separate circuits from the power supply to energize electrode leads and to ensure against any current path being established from a bipolar electrode through bladder tissue to another bipolar electrode.

The Schulman et al. U.S. patent No. discloses an implantable human tissue stimulator with a volatile memory an arrangement which is protected against producing stimulating pulses as a function of unknown parameters in the memory, as a result of inadequate power to the memory from a rechargeable power source, e.g. a rechargeable battery. The arrangement includes voltage sensors, so that when the voltage from the battery drops below a selected level the stimulating circuitry is disconnected from the battery and only the memory is powered. If the voltage from the battery first drops, so that insufficient power is supplied to the memory and thereafter rises, as a result of recharging, to a level sufficient to power the memory, the memory is first reset with known parameter values. Only thereafter when the voltage level reaches the selected level, is the rest of the circuitry, including the stimulating circuitry, reconnected to the battery.

The Keller U.S. Pat. No. 4,203,448 discloses a programmably variable voltage multiplier for an implanted stimulator which includes a free running oscillator that clocks a counter, which produces stimulation control signals at a predetermined counter. An output stage includes transistors, energized by the counter, to issue stimulating pulses having a voltage equal to that across a capacitor in parallel with the output stage. The output capacitor is charged, between output pulses, by successive charge sharing cycles with at least one other capacitor, which is enabled by a stored program word, at a rate determined by the oscillator output cycles.

The Daly U.S. Pat. No. 4,408,608 an implantable stimulator including a capacitor C1 for tuning a coil L1. In the presence of an RF carrier, a capacitor C4 charges through a resistor R2 to the switching threshold of a Schmitt trigger ST2. When the capacitor charges to the threshold level of the Schmitt trigger, its NODATA output goes high to control a reset of the counter and the selection of channel zero.

The Nordling U.S. Pat. No. 4,441,498 discloses an implantable programmable pulse generator that provides electrical stimulation signals to the heart of a patient. The operating parameters of the pulse generator, such as stimulation rate, refractory period duration, and operating mode are programmable by a physician after the pulse generator has been implanted surgically in the patient. An external programmer device includes a transmitter of coded radio frequency (RF) signals. The pulse generator includes a receiver antenna for receiving the coded RF signals. The receiver antenna includes a first wire-wound, air core, planar coil antenna carried on a flexible insulating substrate adjacent an inner wall of a first major side surface of the pulse generator housing and a second wire-wound, air core, planar coil antenna carried on the flexible insulating substrate adjacent an inner wall of a second major side surface of the pulse generator housing. The planar coils are series additive connected to the programmable pulse generator circuit so that the RF signals will be received regardless of the orientation of the pulse generator when it is implanted in the patient. The planar receiver coil antenna provides reliable reception of the RF signal even when the transmitter coil of the programmer is slightly misaligned or tilted with respect to the receiver coil antenna. In addition, the antenna provides a shallow Q factor so that individual high tolerance tuning of the receiver circuits of the pulse generator is not required.

The Borkan U.S. Pat. No. 4,459,989 discloses an electronic tissue stimulator system comprising a plurality of electrodes to be implanted adjacent tissue to be stimulated in a patient. A transmitter transmits stimulation pulses for stimulating the electrodes and programming data defining which of the electrodes are to be stimulated and the electrical polarity of the electrodes relative to one another. A receiver to be surgically-implanted within the patient which receives the stimulation pulses and the programming data, and delivers the energy in the stimulation pulses to the electrodes as defined by the programming data.

The Crosby et al. U.S. Pat. No. 4,532,930 discloses a cochlear implant system including an electrode array (1) comprising multiple platinum ring electrodes in a silastic carrier to be implanted in the cochlea of the ear. A receiver-stimulator (3) containing a semiconductor integrated circuit and other components is implanted in the patient adjacent the ear to receive data information and power through a tuned coil (5) using an inductive link (6) from a patient-wearable external speech processor (7) including an integrated circuit and various components which is configured or mapped to emit data signals from an EPROM programmed to suit each patient electrical stimulation perceptions through testing of the patient and his/her implanted stimulator/electrode using a diagnostic and programming unit (12) connected to the processor by an interface unit (10). The system allows use of various speech processing strategies including dominant spectral peak and amplitude and compression of voice pitch so as to include voiced sounds, unvoiced glottal sounds and prosodic information. Biphastic pulses are supplied to various combinations of electrodes by a switch controlled current sink in various modes of operation. In-place testing of the implant is also provided. Various safety features are incorporated to insure that harmful impulses are not imposed on the patient. Transmission of data is by a series of discrete data bursts which represent the chosen electrode(s), the electrode mode configuration, the stimulating current, and amplitude determined by the duration of the amplitude burst.

The Borkan U.S. Pat. No. 4,612,934 discloses a non-invasive multi-programmable tissue stimulator. The Borkan implantable stimulator includes an external transmitter which transfers power percutaneously through an RF coupling to an implanted stimulator. The implanted stimulator includes a voltage storage circuit and a battery. The voltage storage circuit stores a minimal amount of voltage and electrical energy. The long term voltage stored in this circuit Vm is applied to a comparator and, when voltage Vm is less than a predetermined reference voltage, the implantable stimulator "goes to sleep", that is, the implantable stimulator stops delivering stimulation pulses to the targeted tissue. The implantable stimulator is "woken up" or activated upon receipt of RF coupled commands in a certain sequence.

The Harrison et al. U.S. Pat. No. 4,741,339 discloses an apparatus improving the coupling between an external inductive transmitting coil and an internal inductive receiving coil to transmit power and/or data to the receiving coil from the transmitting coil. The structure includes a coupling coil inductively coupled to the transmitting coil to increase the Q factor and hence the energy transfer between the transmitting coil and the receiving coil.

The Borkan U.S. Pat. No. 4,793,353 discloses an electronic tissue stimulator system comprising a plurality of electrodes to be implanted adjacent tissue to be stimulated in a patient. A transmitter transmits stimulation pulses for stimulating the electrodes and programming data defining which of the electrodes are to be stimulated and the electrical polarity of the electrodes relative to one another. A receiver to be surgically-implanted within the patient which receives the stimulation pulses and the programming data, and delivers the energy in the stimulation pulses to the electrodes as defined by the programming data. Using an internal voltage source, only the programming data need be transmitted which define electrode selection and polarity and stimulation pulse parameters. Physical parameters can be measured and used to modify programming data. Dose periods are defined by programming data and/or a combination of programming data and physical parameter measurements.

The Grevious U.S. Pat. No. 5,168,871 discloses a software-controlled, external programmer for transcutaneously programming and receiving data from an implanted medical device providing enhanced discrimination and detection of pulse-interval-coded signals of interest telemetered out of the implanted medical device from undesirable transient and steady-state noise. The programmer incorporates a detector including an active mixer and a precision tuned active phase shifting network providing low level signal rectification, precise narrow bandpass filtering, and 30 decibels of amplification. At the detector, the received signal is mixed with a phase shifted version of itself to produce a detected DC component which is a function of frequency. The DC response emulates a system with a narrow 25 kHz bandpass filter operating at 175 kHz, but does not share its undesirable transient response. For signals in the reject band, the output produces a signal of the opposite polarity of the signals within the pass bands. Transient noise excites the receiver antenna and produces a ringing response accompanied by components above 400 kHz. The noise response of the antenna stimulates the detector to produce the intended inverted output. As the transient noise amplitude increases, the inverted response increases in amplitude driving the output level further away from the trigger level of a post-detection comparator. Similarly, any steady state noise signal in the reject band will also result in a steady state inverted response that does not trigger the comparator.

The Loeb U.S. Pat. No. 5,312,439 discloses an implantable device having an electrolytic capacitive storage electrode. The device utilizes exposed electrolytic electrodes. Certain capacitors act as filters for a detected data signal.

The Juetter et al. U.S. Pat. No. 5,314,457 discloses a regenerative electrical stimulation device comprising a stimulator portion to be surgically implanted in patients and an external controller portion. The implanted stimulator portion provides electrical stimuli of selected parameters to damaged nerve tissue to stimulate regeneration and/or healing of the damaged nerve tissue. The external controller portion communicates with the implanted stimulator portion to turn the stimulator portion on and off, to change the parameters of the electrical stimuli, to recharge the batteries, and to monitor the status of the batteries. The implanted portion has an antenna coil, a receiver, a programmable control processor, rechargeable batteries, and a passive transmitter. The external controller portion has an antenna coil, a control processor, a transmitter, a receiver for receiving the data passively transmitted by the implantable portion, and a display means.

The Schulman U.S. Pat. No. 5,324,316 discloses an implantable microstimulator which has one or more electrodes immersed in body fluids. The capacitor formed by the body fluids and the electrodes stores 100 microcoulombs of charge. A capacitor is used to tune a coupling circuit which includes a coil. Another capacitor smooths out the ripple in the AC voltage and is used as a filter. The amount of energy received and stored by the microstimulator is controlled by a voltage regulator.

The Miller U.S. Pat. No. 5,350,413 discloses an transcutaneous energy transfer (TET) device comprising a primary winding for placement on or near a skin surface, and a secondary winding for implantation under the skin surface. A field effect transistor (FET) is arranged to switch the primary coil across an external DC power supply. A tuning capacitor is linked to the primary coil whereby the primary coil, when the FET is turned off, will resonate at its natural frequency thereby compensating for drift in component values and reducing power transfer sensitivity to component drift. A bidirectional communications link for the transfer of data across a boundary layer by infrared signals. A plurality of transmitters are arranged in a circular pattern on one side of the boundary layer, whereas a receiver is positioned within the circular pattern along the opposite side of the boundary layer.

The Schulman U.S. Pat. No. 5,358,514 discloses an implantable medical stimulator including a storage capacitor which is charged to a suitable stimulating voltage. Upon discharge, or partial discharge of the charge, as controlled by the closing of a switch and by the setting of a current amplitude limiter. An electrical current pulse flows between two implanted electrodes, thereby stimulating a nerve.

The Schulman U.S. Pat. No. 5,405,367 discloses the use of a capacitor, which is provided by implanted electrodes, on the order of 2 to 30 microfarads.

The Schulman et al. U.S. Pat. No. 5,531,774 discloses an implantable cochlear stimulator having eight output stages, each having a programmable current source connected to a pair of electrodes, designated "A" and "B", through respective output coupling capacitors and an electrode switching matrix. An indifferent electrode is connected to each output stage by way of an indifferent electrode switch. An output mode register controls the switching matrix of each stage, as well as the indifferent electrode switch, to configure the electrodes for: (1) bipolar stimulation (current flow between the pair of electrodes of the output stage), (2) monopolar A stimulation (current flow between the "A" electrode of the output stage and the indifferent electrode), (3) monopolar B stimulation (current flow between the "B" electrode of the output stage and the indifferent electrode), or (4) multipolar stimulation (current flow between the "A" or "B" electrode of one output stage and the "A" or "B" electrode of another output stage). The mode register is set by way of a command word, transmitted to the stimulator from an external wearable system as part of a data frame. The voltage at the "A" and "B" electrode of each output stage may be selectively telemetered to the wearable system, as may the current flow through the indifferent electrode, thereby facilitating a measurement of the electrode impedance. The "A" and "B" electrodes of each output stage may be selectively shorted through a high or low resistance in order to discharge the output coupling capacitors.

The Grevious U.S. Pat. No. 5,562,714 discloses a regulator in a transmitter of a medical device system including circuitry for sensing the strength of a magnetic field generated from a transmitting antenna of the antenna and circuitry responsive to the strength of the magnetic field sensed for variably loading the magnetic field to regulate the strength of the magnetic field.

SUMMARY OF THE INVENTION

It is an objective of the present invention to provide a partially implanted medical device system, wherein the subcutaneous receiver and external transmitter form a closed-loop, inductively coupled RF energy transfer system, whereby the transmitted RF power is adjusted up or down by the receiver as a function of received vs. required power, via commands up-linked by the receiver to the transmitter.

Another aspect of the present invention is to provide a partially implanted tissue stimulator system, wherein a subcutaneous receiver incorporates the required faculties to autonomously control all stimulation parameters after it has been programmed only once. The stimulation parameters controlled by the receiver are pulse amplitude, width and frequency, plus identification of the electrodes to be enabled and their respective polarity.

Another aspect of the present invention is to provide an RF coupled neural stimulator system wherein the subcutaneous receiver is capable of maintaining the programmed pulse amplitude constant within a significant range of variation in the coupling distance between the transmitting and receiving antennas. This is accomplished by incorporating within the receiver: 1) a voltage regulator to provide a constant voltage supply to the receiver's output circuit, 2) comparators for comparing the voltage received, 3) a microcontroller and memory which manage the input lines to a D/A converter, 4) the D/A converter providing a negative output voltage corresponding to the statue of its input lines, and, 5) a four (4) channel multiplexer used: a) during the stimulus pulse, to pass the negative output voltage of the D/A converter to the electrode(s) which are programmed to a negative polarity and, b) during the stimulus pulse, to switch to the positive rail (VDD) those electrodes which are programmed positive.

Another aspect of the present invention is to provide a subcutaneous receiver which only needs to be. programmed once for each program modification (instead of for each stimulus pulse as in prior art devices), thus reducing the risk of inappropriate stimulation in an electrically noisy environment.

Another aspect of the present invention is to provide an RF coupled neural stimulator system wherein the subcutaneous receiver is capable of: 1) detecting, demodulating and memorizing in a non-volatile memory, data defining all stimulation values, 2) autonomously regulate, according to the memorized stimulating values, all stimulation functions such as amplitude, rate, pulse width, amplitude ramp-up time at the start of stimulation, amplitude ramp-down time when stimulation ceases, and electrode polarity. This is accomplished by incorporating within the receiver: a) an amplifier/filter to extract from ambient electrical noise data pulses down-linked by the transmitter and b) a microcontroller which demodulates the data, stores their values in the appropriate memory locations, and regulates, according to the data, the stimulus pulse amplitude and width, rate, amplitude ramp-up time, amplitude ramp-down time, and electrode polarity.

Still another aspect of the present invention is to provide a subcutaneous receiver which stores the programmed stimulation values in a non-volatile memory, thus eliminating the need to reprogram the receiver each time RF transmission ceases and later restarts, such as when the patient replaces the battery in the external RF transmitter.

A further aspect of the present invention is to provide a subcutaneous receiver capable of autonomously regulating pulse amplitude within a variable range of coupling distance between the transmitting and receiving antennas so that precise positioning of the transmitter relative to the receiver is not required. The receiver incorporates a receiving inductor to gather RF energy. The inductor is coupled to a rectifier, the rectifier is coupled to a high voltage storage capacitor and the capacitor is coupled to a voltage regulator which outputs a lower but constant voltage. The regulator powers a digital to analog converter whose voltage output (pulse amplitude), duration (pulse width) and duty cycle (pulse frequency) is managed by a microcontroller, a microprocessor or a logic circuit.

According to the present invention there is provided an implantable, electrically operated medical system comprising an implantable radio frequency (RF) receiver and an external RF transmitter. The receiver has a receiving antenna and electronic circuitry coupled to the receiving antenna and includes a microcontroller having an output, a non-volatile memory coupled to the microcontroller and an implanted, electrically and autonomously operated medical device is coupled to the output of the microcontroller. The external RF transmitter has a power source and a transmitting antenna. The receiver further includes high/low voltage sensing circuitry coupled to the microcontroller for regulating the power transmitted by the transmitter, whereby, RF energy can be transmitted by the transmitter and coupled into the receiver where it is used exclusively to power the implanted medical device and the level of RF energy transmitted by the transmitter is controlled by the level of voltage detected by the high/low voltage sensing circuitry. The transmitter is also used to: a) program into the memory of the implanted device (receiver) its operating values; b) start and stop delivery of medical therapy by the implanted device, c) interrogate the operating values of the implanted device, and d) interrogate physiological parameters which are measured by the implanted device. When the implanted device is an electrical stimulator (i.e., neural stimulator or cardiac pacemaker), because the implanted device incorporates a voltage regulator to maintain a constant voltage supply to the receiver electronic circuitry and because the implanted device incorporates protocol for regulating pulse amplitude from a D/A converter, the stimulating pulse amplitude is insensitive to normal changes in coupling distance between the antenna/inductor of the transmitter and the antenna/inductor of the receiver. Also, because the receiver includes a non-volatile memory to store the operating values of the implanted device, if transmission of RF energy ceases and later is restored (i.e. to change the transmitter's battery) the implanted device can resume stimulation at the previous values without reprogramming.

The high/low voltage sensing circuitry can comprise comparators, namely "high" and "low" voltage comparators coupled to the microcontroller for detecting if the induced voltage level is below a first low threshold, above a second higher threshold or is in between the two thresholds. The high/low voltage sensing circuitry also can be realized by a voltage divider including two series connected resistors with the junction between the resistors coupled to the microcontroller A/D input.

The voltage regulator is constructed and arranged to maintain a constant voltage supply to the electronic circuitry and, with the D/A converter being operable to regulate pulse amplitude, the stimulating pulse amplitude of the pulses supplied from the D/A converter to the implanted medical device is insensitive to normal changes in coupling distance between the transmitter antenna and the receiver antenna.

BRIEF DESCRIPTION OF THE DRAWINGS

FIG. 3A are graphs of voltage, at different points in the electronic circuits for the transmitter and for the receiver versus "ON" time and "OFF" time of a control transistor in the transmitter electronic circuit.

FIG. 3B are graphs of transmitted RF energy bursts and of receiver commands up-linked to the transmitter versus time.

DESCRIPTION OF THE PREFERRED EMBODIMENT(S)

Figure 1:
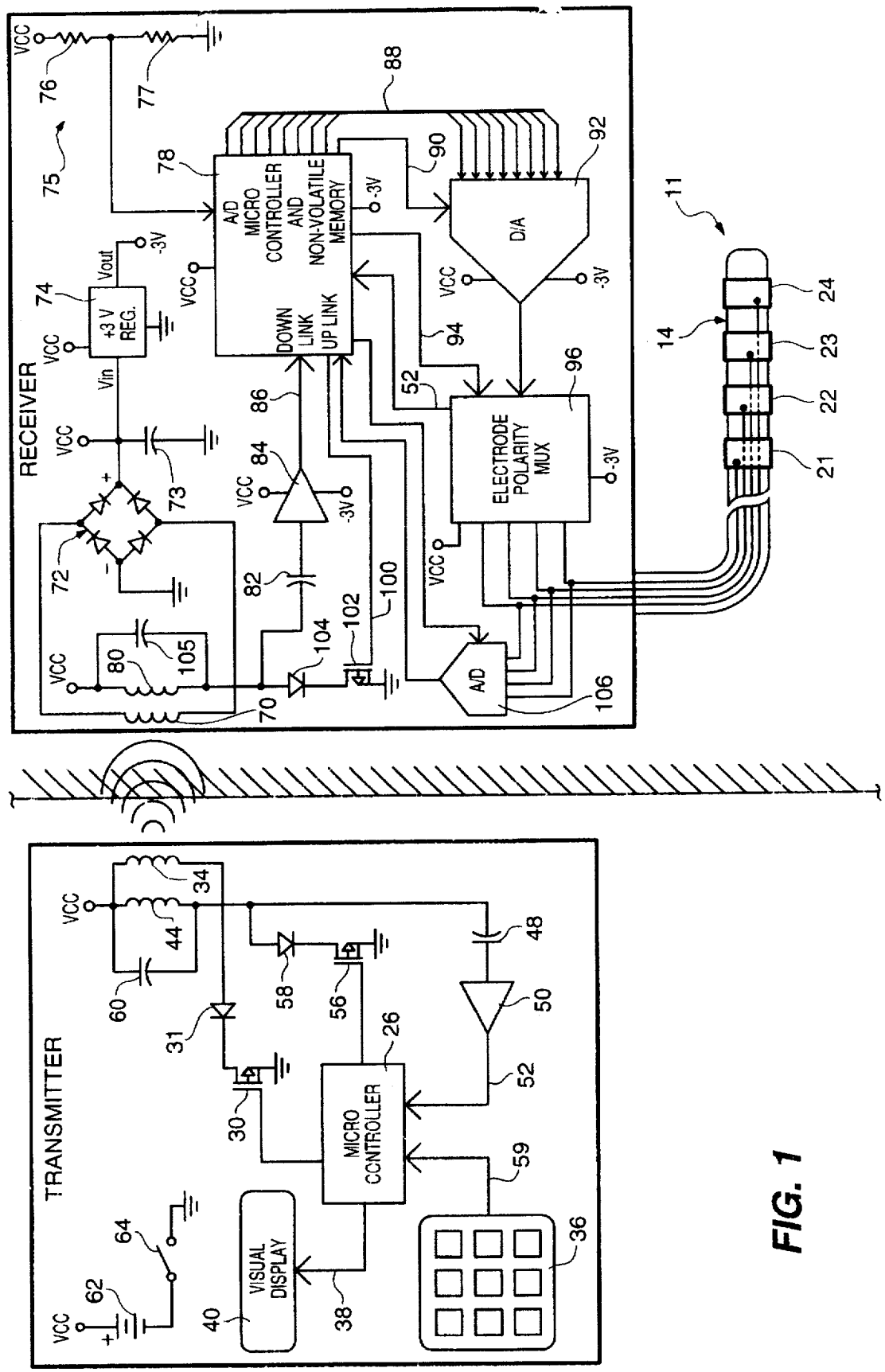
FIG. 1 is a block electrical schematic circuit diagram of an implanted device and of a power transmitting device which is adapted to be positioned closely adjacent the implanted device, both being constructed according to the teachings of the present invention.

Referring now to FIG. 1, which is a block electrical schematic diagram of the implantable, electrically operated medical system, there is illustrated a receiver 10 including a tissue stimulator 11 as the implanted medical device. However, it will be understood that the implanted medical device can be any other medical device which requires electrical power for long periods of time.

The system further includes an external RF transmitter 12 which is capable of being RF coupled to the subcutaneously implanted receiver 10 which is connected to an implanted lead 14 of the tissue stimulator 11. The lead 14 has, at its distal end 16, stimulating electrodes 21-24. These electrodes 21-24 are implanted adjacent to the target tissue to be stimulated (i.e., a specific nerve or nerve bundle, or a specific area of the brain, or a specific muscle within the human body).

Referring again to FIG. 1, the major components of the transmitter 12 are a microcontroller 26 which is used to: 1) enable, via line conductors 28, an N channel transistor 30 which passes electric current through a diode 31 and a line conductor 32 to an inductor 34 to cause RF energy to be transmitted; 2) respond to inputs from a keyboard 36; 3) output alpha-numeric data, via line conductors 38, to a visual display 40 to exhibit the receiver's programmed values and on/off status; 4) to decode data up-linked by the subcutaneous receiver 10, picked-up by an inductor 44, and transmitted via a line conductor 46, a capacitor 48, an amplifier/filter 50 and a line conductor 52 to the microcontroller 26; 5) down-link to the receiver 10 through the antenna/inductor 44 relatively low RF energy pulses representing operating values and commands to the subcutaneous receiver 10, via a line conductor 54, a transistor 56, a diode 58 and the inductor 44. The keyboard 36 is coupled to the microcontroller 26 by line conductors 59 and is used to start or stop stimulation, increase or decrease any one of the receiver's stimulation parameters, change receiver's electrode polarity, or cause the receiver 10 to measure the impedance of the electrodes 21-24. The display 40 is used to exhibit the stimulation values, stimulation on/off status and the impedance of the electrodes 21-24. A capacitor 60 is used to tune the inductor 44 to a desired down-link frequency.

The inductor 44, the capacitor 48 and the amplifier/filter 50 are used to detect RF pulses up-linked by the receiver 10 representing commands for stimulating values and supply them via line conductor 52 to the microcontroller 26.

A battery 62 is used to power the RF transmitter 12 via an on/off switch 64 and to power the subcutaneous receiver 10 via the closed-loop RF coupled system.

The major components of the subcutaneous receiver 10 are an RF receiving inductor 70, a rectifier 72, a high voltage storage capacitor 73, a voltage regulator 74, a voltage divider 75 comprising resistors 76 and 77 with a junction between them connected to an A/D port of the microcontroller 78 for sensing a voltage at the junction which is related to the voltage stored at capacitor 73 which becomes the VCC supply for the receiver. The voltage at the junction represents the level of RF power captured by the receiver, and then, depending on the voltage sensed, the microcontroller 78 is caused to send, a decrease, or a leave as is, signal to the transmitter 12 (no signal sent indicates that the transmitted RF power must be increased), and a D/A converter 106 is capable of delivering voltage or current pulses to electrodes 21-24 through a multiplexer 96.

These components are used to: 1) receive at the microcontroller 78, via an inductor 80, a capacitor 82, an amplifier/filter 84 and a line conductor 86, specific data defining stimulation values, electrode selection and polarity, all of which are programmed into an erasable/reprogrammable non-volatile memory in or associated with the microcontroller 78; 2) regulate, via a voltage bus 88 and an enable line 90, the output voltage and on/off duration, respectively, of a D/A converter 92; 3) select, via a line conductor 94 from the microcontroller 78 to a multiplexer 96, for passing to those electrodes 21-24 which are selected as having a negative polarity the output of the D/A converter 92 during the stimulus pulse and which electrodes 21-24 will be positive (switched to VDD); 4) up-link, via a line conductor 100, a transistor 102, a diode 104, and the inductor 80 tuned which is tuned with a capacitor 105 for up-linking to the transmitter's antenna/inductor 34, (a) data defining the receiver's stimulating values, measured lead impedance, and programmed electrode/polarity combination, (b) commands defining if the transmitter's RF power needs to be increased, decreased or maintained at the present level; 5) command an A/D converter 106 coupled to the electrodes 21-24 and to the microcontroller 78 to measure the impedance across the electrodes 21-24.

Energy is transferred from the battery 62 in the transmitter 12 to the capacitor 73 in the receiver 10 via a closed-loop RF coupled system using the transmitter 12.

The transmitter 12 under management of microcontroller 26 broadcasts pulsed RF power by first switching on the transistor 30 for a predetermined period of time to cause the inductor 34 to saturate. Then transistor 30 is switched off causing the electric field across the inductor 34 to collapse, resulting in the inductor 34 generating a self-induced voltage far exceeding the voltage of the battery 62.

During the self-induced voltage state, the diode 31 becomes reverse-biased allowing the voltage at the inductor 34 to safely swing below ground potential.

The mean RF energy transmitted to the receiver 10 is regulated by the microcontroller 26 by adjusting both the "ON time" and the "OFF time" of the transistor 30 as shown in FIG's. 2 and 3A. Microcontroller 26 transmits these RF bursts for a fixed period of time and then rests for a few milliseconds to allow the receiver to up-link commands as shown in FIG'S. 2 and 3B, indicating if the transmitted RF power needs to be increased, decreased or maintained at the present level. Then immediately, microcontroller 26 responds by adjusting the transmitted RF power, higher or lower, depending on whether the up-linked command was, "decrease", OK or no up-link ("increase").

If no up-link is detected, transmitter 12 assumes not enough power is being coupled into the receiver 10 and automatically increases the mean RF power to the next higher level.

If the "OK" command is received, then the transmitter 12 continues to broadcast at the same mean RF power.

If the "decrease" command is received, then the transmitter 12 decreases the mean RF power transmitted to the next lower level.

Figure 2:
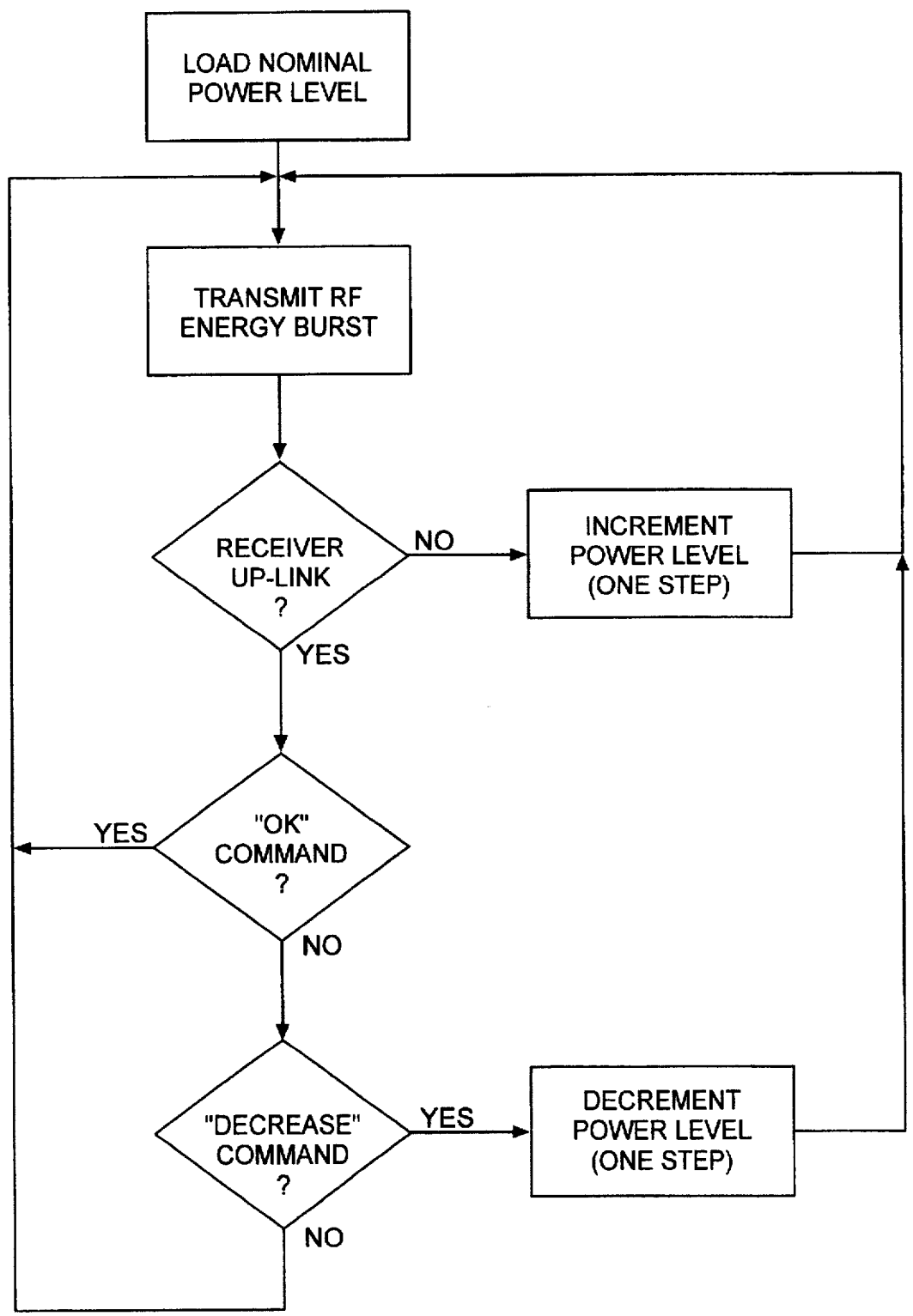
FIG. 2 is a flow chart of the power regulation protocol carried out by the microcontroller in the receiver for adjusting the power supplied to the implanted medical device relative to the RF pulses (energy bursts) received by the receiver.

FIG. 2 is a flow chart of the power regulation protocol carried out by the microcontroller 78 in the receiver 10 for adjusting the power supplied to the implanted medical device 11 relative to the RF pulses (energy bursts) received by the receiver inductor 70.

FIG. 3A are graphs of voltage, at the gate of transistor 30 and between the diode 31 and the inductor 34 in the electronic circuit for the transmitter and at the capacitor 73 in the electronic circuit for the receiver 10 versus "ON" time and "OFF" time of the control transistor 30 in the electronic circuit for the transmitter 12.

FIG. 3B are graphs of transmitted RF energy bursts from the antenna/inductor 34 and of digital commands up-linked from the receiver 10 via antenna/inductor 80 to the transmitter 12 versus time.

The receiver 10 is used to deliver, via the lead 14 and the electrodes 21-24, stimulating pulses of the frequency, amplitude and width defined by the program stored in the receiver's non-volatile memory. Therefore, there is no need for the transmitter 12 to transmit, on a real time basis as is required in prior art devices, the values of each stimulation pulse.

According to the teachings of the present invention, transmission of high energy RF power is used only to couple into the receiver 10 the operating power requested by the receiver 10 according to: (a) the coupling distance and alignment between the transmitting inductor 34 and the receiving inductor 70 and (b) the stimulation pulse: amplitude, width and rate plus the impedance across the electrodes 21-24.

If the transmitting inductor 34 is moved away from the receiving inductor 70 for more than a few seconds, the capacitor 73 will discharge and the receiver 10 will stop stimulating. However, since the stimulation values are safely retained by the non-volatile memory of the microcontroller 78 in the receiver 10, upon restoration of transmission of high energy RF power by the close placement of the inductor 34 to the receiving inductor 70, the stimulation therapy will automatically resume at the previous stimulation values without the need for reprogramming of the receiver.

Figure 4:
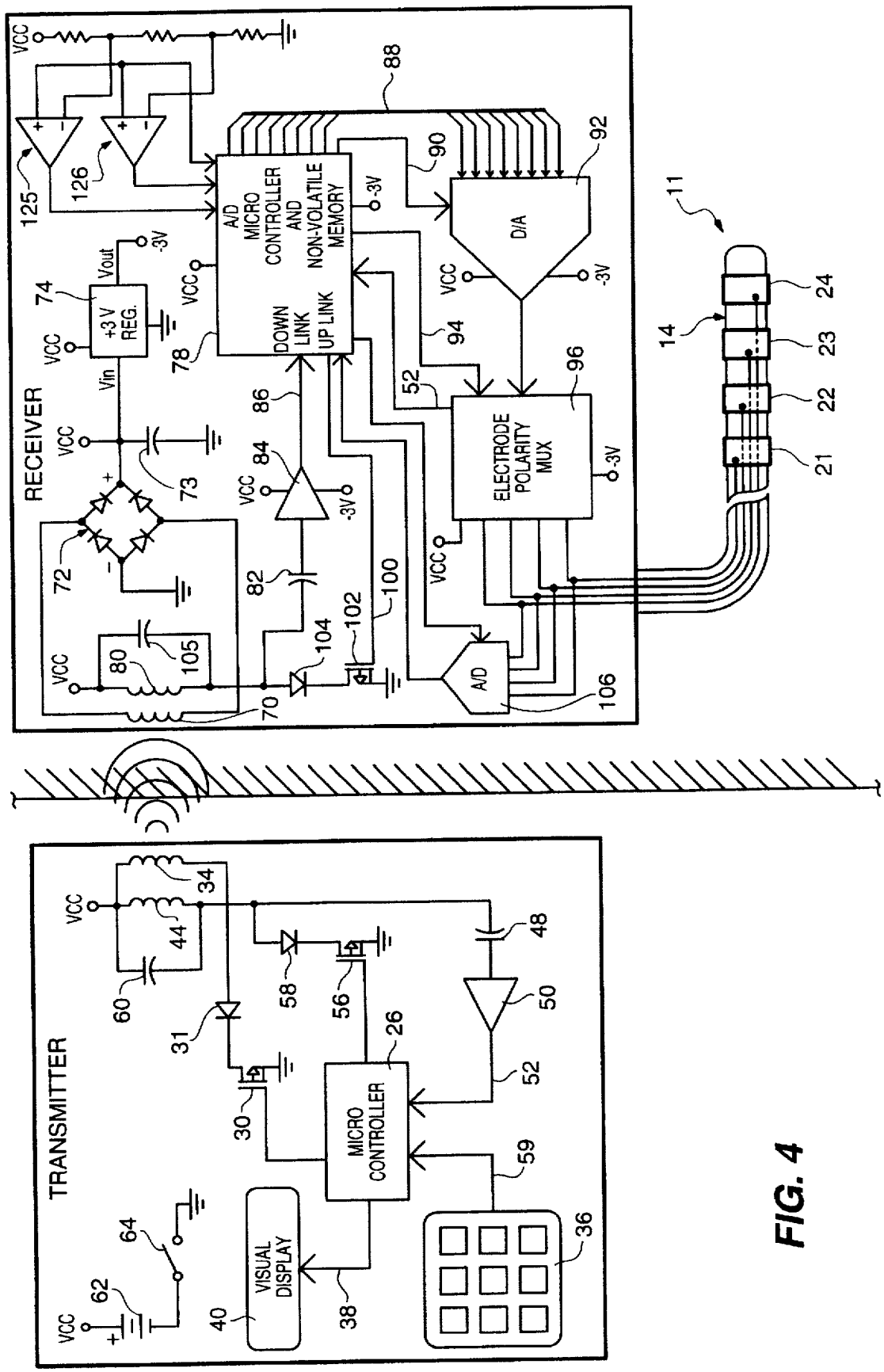
FIG. 4 is a block electrical schematic circuit diagram of an implanted device and of a power transmitting device which is adapted to be positioned closely adjacent the implanted device, similar to the view shown in FIG. 1 but showing comparators instead of a voltage divider connected to a microcontroller in the implanted device, both devices being constructed according to the teachings of the present invention.

In FIG. 4 there is illustrated a modified receiver 10 wherein the voltage divider 75 connected to the microcontroller 78 is replaced by two comparators 125 and 126 connected as shown with their positive (+) inputs connected to a reference voltage which can be supplied by the microcontroller 78 as illustrated. The comparators 125 and 126 sense an upper voltage related to the supply voltage, VCC, and a lower voltage related to the supply voltage, VCC, and compare those voltages with a reference voltage and then cause the microcontroller 78 to send, an increase, or a leave as is, signal to the transmitter 12.

From the foregoing description, it will be apparent that the closed-loop, RF-coupled implanted medical device of the present invention has a number of advantages, some of which have been described above and others of which are inherent in the invention. Also it will be understood that modifications can be made to the closed-loop, RF-coupled implanted medical device described above without departing from the teachings of the present invention. Accordingly, the scope of the invention is only to be limited as necessitated by the accompanying claims.

I claim:

1. An implantable, closed-loop, electrically operated medical system comprising: (a) an implantable radio frequency (RF) receiver coupled to an implanted, electrically and autonomously operated medical device; and, (b) an external RF transmitter which is used to supply said implanted medical device with electrical power; said receiver having a RF power receiving antenna, electronic circuitry coupled to said receiving antenna and including means for converting said received RF power into a D.C. voltage, a microcontroller having output and input means, a non-volatile memory coupled to said microcontroller, high/low voltage sensing means coupled to said microcontroller, means for up-linking commands to said transmitter to decrease or leave as is, said transmitted RF power, said implanted medical device being coupled to said output means of said microcontroller; and said transmitter having a power source, a RF power transmitting antenna, means for detecting and decoding commands up-linked by said receiver, and means for regulating said transmitted RF power level in response to said up-linked signals whereby, RF energy or power can be transmitted by said transmitter and coupled into said receiver where it is used exclusively to power said implanted medical device and the level of RF power transmitted by said transmitter is controlled by the level of voltage detected by said high/low voltage sensing means of said receiver.

2. The medical system of claim 1 wherein said electronic circuitry includes a rectifier coupled between said receiving antenna and said microcontroller.

3. The medical system of claim 2 wherein a positive DC output of said rectifier is coupled to a storage capacitor and the voltage level at said storage capacitor becomes a VCC supply voltage for said receiver.

4. The medical system of claim 1 wherein said electronic circuitry includes a multiplexer coupled between said microcontroller and the implanted medical device.

5. The medical system of claim 1 wherein said electronic circuitry includes a D/A converter coupled between said microcontroller and the implanted medical device, said D/A converter being capable of deliverinq stimulus pulses having either a constant current or a constant voltage.

6. The medical system of claim 1 wherein said electronic circuitry includes an A/D converter coupled between the implanted medical device and said microcontroller.

7. The medical system of claim 1 wherein said means for up-linking commands includes up-link circuitry coupled to said microcontroller for up-linking data to said transmitter.

8. The medical system of claim 1 wherein said transmitter includes a second microcontroller and down-link circuitry coupled to said second microcontroller for down-linking data to said receiver.

9. The medical system of claim 1 wherein said non-volatile memory is an erasable, reprogrammable non-volatile memory.

10. The medical system of claim 1 wherein microcontroller has an A/D input and said high/low voltage sensing means comprise a voltage divider defined by two resistors and a junction between said two resistors coupled to said A/D input of said microcontroller for sensing a voltage at the junction which is related to a supply voltage named VCC, said microcontroller using the voltage sensed by said voltage divider to cause said microcontroller to send, an increase, or a leave as is, signal to said transmitter.

11. The medical system of claim 1 wherein said transmitter comprises means for: (a) programming into said non-volatile memory operating values for controlling the functions of said implanted medical device; (b) starting and stopping delivery of medical therapy by said implanted medical device, and (c) interrogating said medical device to determine the actual operating values of said medical device.

12. The medical system of claim 1 wherein, when new operating values are programmed into said receiver by said transmitter, said operating values are automatically stored in said non-volatile memory, so that if transmission of RF power ceases and later is restored, said implanted medical device can resume operation at the previous values without reprogramming.

13. The medical system of claim 1 wherein said implanted medical device is a neural stimulator.

14. The medical system of claim 1 wherein said implanted medical device is a cardiac pacemaker.

15. The medical system of claim 1 wherein said high/low voltage sensing means comprise first and second comparators for sensing an upper voltage related to a supply voltage named VCC, and a lower voltage related to the supply voltage, VCC, and comparing those voltages with a reference voltage and then causing the microcontroller to send, an increase, or a leave as is, signal to said transmitter.

16. The medical device of claim 1 wherein said microcontroller in said receiver includes an A/D converter input for measuring and comparing a supply voltage, VCC against at least two predetermined thresholds, said VCC voltage representing the level of RF power reaching said receiver.

17. The medical device of claim 1 wherein said microcontroller is coupled to an inductor for up-linking signals to said transmitter for increasing or leaving as is said transmitted RF power level.

18. The medical device of claim 1 wherein said transmitter includes control means responsive to said up-link signals to decrease, maintain or increase the level of transmitted RF power.

19. The medical system of claim 1 wherein said implanted medical device comprises (a) an insulated lead having at least two conductors each connecting contacts between its proximal and distal ends, and (b) the contacts at the distal end forming electrodes used for electrical stimulation of adjacent tissue.

20. The medical system of claim 19 wherein said electronic circuitry further includes (a) means for measuring the voltage which develops at said electrodes during delivery of said electrical stimulus pulses of a known constant current value, said means for measuring voltage having an output signal connected to said microcontroller; and (b) means for calculating the electrode impedance by dividing the voltage sensed over a known constant current value.

21. The medical system of claim 1 wherein said receiver, in response to said received level of RF power, up-links signals to said transmitter to cause the level of transmitted RF power to be (a) decreased, (b) maintained, or (c) increased in the absence of any up-link signal, so that transmitted RF power is a function of received RF power; said transmitter and said receiver forming a closed-loop, auto-regulated RF power system for optimizing the life of a battery in said transmitter by maintaining transmitted RF power at the minimum level necessary for dependable and effective receiver operation, regardless of the operating values programmed into said medical device.

22. An implantable medical device system comprising an implantable medical device, an implantable receiver coupled to and associated with said medical device and a transmitter;

said transmitter having means for transmitting a burst of RF energy to said implanted receiver;

said transmitter having means for receiving information from said implanted receiver;

said receiver having means for receiving said RF burst of energy from said transmitter and for using said burst of energy to supply an electrical signal to said implanted medical device;

means for transmitting to said transmitter information regarding the amount of RF energy needed to supply adequate power to said receiver and means in said transmitter for adjusting the amount of RF energy transmitted to said receiver depending upon said information received from said receiver.

23. The implantable medical system of claim 22 wherein said receiver includes means for determining if the power supplied to said receiver is sufficient to operate the receiver circuitry dependent upon the needs of the patient and means for transmitting to the transmitter information regarding whether or not the transmitted RF power received should be increased or decreased or stay the same.

24. The medical system of claim 22 wherein said transmitter includes means for adjusting the amplitude of a pulse of RF energy transmitted in response to said information received from said receiver thereby to increase or decrease the RF energy transmitted from said transmitter to said receiver.

25. The medical system of claim 22 wherein said transmitter includes means for adjusting the duration of a pulse of RF energy transmitted in response to said information received from said receiver thereby to increase or decrease the RF energy transmitted from said transmitter to said receiver.

* * * * *